(12) United States Patent
Nilsson

(10) Patent No.: US 7,371,007 B2
(45) Date of Patent: May 13, 2008

(54) METHOD FOR PRE TREATMENT VERIFICATION IN RADIATION THERAPY

(76) Inventor: Gorgen Nilsson, Gryningsvagen 47, Storvreta (SE) S-743 32

( * ) Notice: Subject to any disclaimer, the term of this patent is extended or adjusted under 35 U.S.C. 154(b) by 216 days.

(21) Appl. No.: 10/551,184

(22) PCT Filed: May 21, 2004

(86) PCT No.: PCT/SE2004/000781

§ 371 (c)(1),
(2), (4) Date: Sep. 29, 2005

(87) PCT Pub. No.: WO2004/103145

PCT Pub. Date: Dec. 2, 2004

(65) Prior Publication Data

US 2006/0203967 A1    Sep. 14, 2006

Related U.S. Application Data

(60) Provisional application No. 60/472,773, filed on May 23, 2003.

(30) Foreign Application Priority Data

May 23, 2003    (SE) .................................... 0301508

(51) Int. Cl.
*G01D 18/00* (2006.01)
(52) U.S. Cl. ...................... 378/207; 378/65; 378/95
(58) Field of Classification Search ............ 378/65–69, 378/91, 94, 95, 108–112, 162–165, 207
See application file for complete search history.

(56) References Cited

U.S. PATENT DOCUMENTS

| | | | |
|---|---|---|---|
| 5,511,107 A | 4/1996 | Sliski | 378/207 |
| 6,712,508 B2* | 3/2004 | Nilsson et al. | 378/205 |
| 2005/0077459 A1* | 4/2005 | Engler et al. | 250/252.1 |

OTHER PUBLICATIONS

International Search Report of PCT/SE2004/000781, mailed Oct. 29, 2004.
Agazaryan et al., "Three-Dimentional Verification For Dynamic Multileaf Collimated IMRT", Proceedings of the 22$^{nd}$ Annual EMBS Int Conf, Jul. 23-28, 2000.
Jursinic et al., "A 2-D Diode Array and Analysis Software for Verification of Intensity Modulated Radiation Therapy Delivery", Apr. 22, 2003, Med. Phys. 30(5).
Bjork et al., "Comparitive Dosimetry of Diode and Diamond Detectors in Electron Beams for Intraoperative Radiation Therapy", Aug. 15, 2000, Med. Phys. 27(11), Nov. 2000.
Chuang, et al., "Investigation of the use of Mosfet for Clinical IMRT Dosimetric Verification", Mar. 22, 2002, Med. Phys, 29(6), Jun. 2002.
Shi et al., "Important Issues Regarding Diode Performance in Radiation Therapy Application", Proceedings of the 22$^{nd}$ Annual EMBS Int Conf, Jul. 23-28, 2000.

(Continued)

*Primary Examiner*—Jurie Yun
(74) *Attorney, Agent, or Firm*—Nixon & Vanderhye P.C.

(57) ABSTRACT

Dose distribution is measured in a patient-shaped phantom with high accuracy for radiation therapy treatment verification. A detector configuration in such a phantom and improvements in measurement methodology enable application of correction factors in an accurate way.

24 Claims, 4 Drawing Sheets

OTHER PUBLICATIONS

Soares, et al., "Dosimetry of Beta-Ray Ophtalmic Applicators: Comparison of Different Measurement Methods", Jan. 31, 2001, Med. Phys. 28(7), Jul. 2001.

PCT International Preliminary Examination Report dated Sep. 2005 issued in International Application No. PCT/SE2004/000781.

International Application No. PCT/SE03/00725 filed May 6, 2002, Görgen Nilsson.

Periodical: Medical Physics, vol. 30, No. 1, Jan. 2003.

Advertisement: MapCHECK, IMRT QA . . . No Film, Sun Nuclear Corporation.

Chuang et al., Investigation of the use of MOSFET for clinical IMRT dosimetric verification, Med. Phys. 29(6), Jun. 2002, pp. 1109-1115.

* cited by examiner

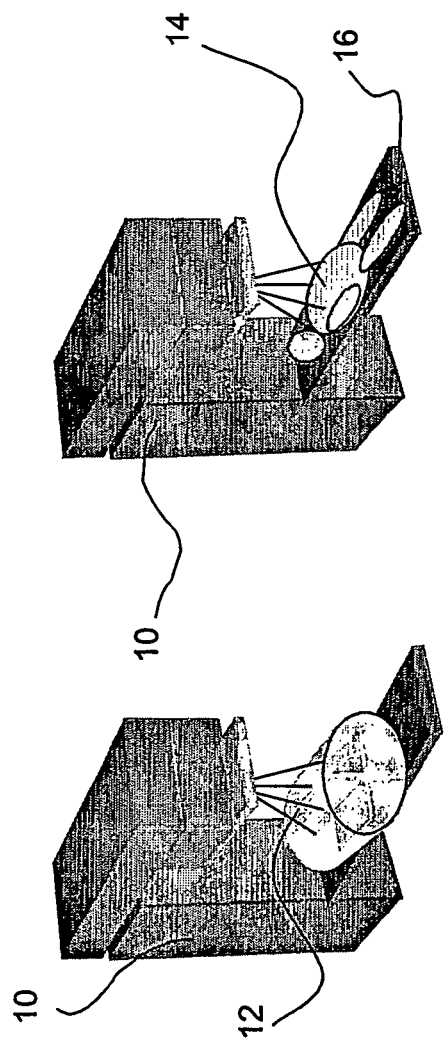
Fig. 1a
Fig. 1b
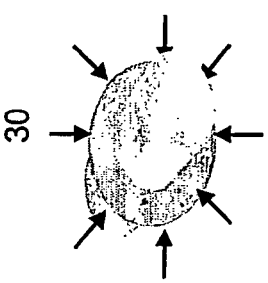
Fig. 2
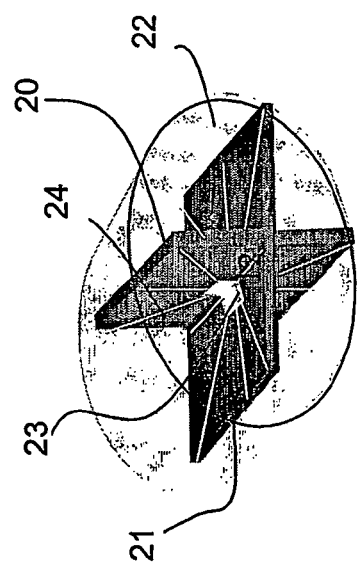
Fig. 3

METHOD FOR PRE TREATMENT VERIFICATION IN RADIATION THERAPY

This application is the US national phase of international application PCT/SE2004/000781, filed 21 May 2004, which designated the U.S. and claims priority of SE 0301508-8, filed 23 May 2003, and U.S. 60/472,773, filed 23 May 2003, the entire contents of each of which are hereby incorporated by reference.

TECHNICAL FIELD

The present invention relates generally to radiation therapy treatment verification. In particular the invention pertains to methods, a detector configurations, a detector and a computer readable medium for verifying that a patient specific cancer treatment using radiation therapy, and in particular intensity modulated radiation therapy, is delivered as planned.

BACKGROUND

Radiotherapy has been used to treat cancer in the human body since early 1900. Even though radiation of cancer tumours is known to be efficient, mortality rate for many cancers remained virtually unchanged for a long time. The major reasons for this have been the inability to control the primary tumour or the occurrence of metastases. Only by improving the local control may the treatment be more effective.

In the last years Treatment Planning Systems, TPS, in Radiation Therapy have developed extensively and are now able to take into account the anatomy of the specific patient, and in a time efficient way plan a more optimised treatment for each individual patient including a homogenous dose to the target and a minimum dose to risk-organs.

The treatment technique to deliver this optimised treatment is more complicated than conventional treatments because each field must be modulated laterally in intensity and thereby compensate for the patients contour and anatomic heterogeneity. The technique is called IMRT—Intensity Modulated Radiation Therapy. The delivery can be done using compensators, i.e., filters individually made for each projection, that reduce the intensity to a predefined level in each part of the field due to attenuation of the primary photon beam. However when using several projections (4-8), each projection requiring individual compensators, this technique is time-consuming and requires a lot of effort. Additionally the attenuation of the beam in the filter causes an unwanted change of the beam's spectral distribution, thereby complicating the whole process. The most common way to deliver IMRT is therefore using the MLC (Multi Leaf Collimator) a device that consists of thin blocks (collimator-leafs) that can be individually positioned to block a small part of the field and thereby shape the beam in the lateral direction into various irregular shapes. In each projection, the collimator-leafs are moved during the treatment and thereby various parts of the cross-section of the beam are irradiated during various times, i.e., the dose distribution is modulated. The conformity of the dose distribution to the tumour can be further improved using even more sophisticated techniques also changing the projection while the beam is on, e.g., ARC-therapy.

In conventional therapy it is sufficient to make periodic verification on the level of the dose distribution on the central axis and in a few points off-axis to verify the beam-symmetry and beam-flatness. The new treatment technique is complicated and involves the transfer of information between several systems and therapy system sub-modules, and the cross section of the beam is individualized for each projection on each patient, thereby extended quality assurance is required.

The fundamental function of IMRT, of building-up the dose in the field by blocking some parts of it longer than others often increases the beam-on time, and thereby the dose to the area outside the field increases. In IMRT, accurate measurement of the dose to the areas outside the field is thereby more important than in conventional treatment, a requirement that further increases the demands in the measurement process.

Good quality control procedures in a radiation therapy clinic treating with IMRT technique include:
 Machine specific quality assurance, e.g., stability check of the dose rate, time for the treatment system to stabilise, mechanical QA of the MLC etc. before the treatment machine is accepted to be used for treatments.
 Pre treatment verification—Measurement performed on each individual treatment plan, before the patient is given the first treatment fraction, to verify the ability to deliver the treatment accurately.
 Patient dosimetry or in vivo dosimetry—Verification of the delivered dose to the patient during the actual treatment, see the Swedish patent application 0201371-2.

Pre treatment verification can be done for each individual projection using a 2D detector in a flat phantom positioned perpendicular to the beam or it can be done for one treatment occasion including all projections using a body phantom with detectors. Both methods have implementations using traditional measurement techniques and both of them have important limitations both in methodology and in measurement accuracy.

The shortcoming of the first method is:
 Complicated and time-consuming to verify each projection individually rather than the total contribution from all projections in one comparison.
 Unnecessary efforts invested in correcting minor errors per projection that would have shown to be neglectable if all projections could be totalled.
 The verification excludes errors in gantry angle and collimator rotation since the device is either attached to the gantry or the gantry rotation is not used during verification.
 It is not useful in ARC-therapy (described above).
 Lack of time resolution in the measurements disables the possibility to analyse the course of a measured deviation, e.g. in sub fields or segments of a field without updated measurement. Additionally there is no possibility to distinguish whether a dose is delivered when expected during the respiratory cycle.

The first method has been implemented in a product, MapCheck available from Sun Nuclear INC., consisting of a matrix of diodes where each detector integrates the dose during the delivery of one projection. Measuring at one depth in the same beam direction simplifies most of the requirements on the detector to similar to those in traditional measurements. However the requirement to measure with high accuracy outside the primary field, described above, raises several demands on the detectors, and one of the hardest to fulfil for semiconductors is energy independency.

The second method simulates the patient on the couch using a body shaped or head-and-neck shaped plastic-phantom, see U.S. Pat. No. 6,364,529 [MED TEC IOWA INC (US)), with some kind of detectors inserted into it. The phantom that is placed on the couch, without connection to the gantry rotation, can be irradiated similar to a patient in any relevant projection. Thereby the delivered dose from all projections can be measured at any point inside the phantom. Error in delivery, e.g., in MLC position, gantry angle, collimator rotation etc., will cause similar dose discrepancy in the phantom as in the patient. Until now this method has been used with radiological films placed inside the phantom in the direction of the beam and a few point-detectors. The film measures thereby in 2-dimension (2D) along the beam with high spatial resolution. However, across the field, where the beam is modulated, the method is limited to measure along the film (1D). The main reason for the orientation of the film is the shortcoming of film as a detector. The response of radiological films depends on several parameters e.g. direction of radiation, energy, pressure (the pressure on the film at exposure), development process, fading, linearity etc. Additionally, film is an integrating detector so that the film-data has no time resolution, and thereby, analyses of the cause of a deviation between measurement and the treatment plan often become more or less impossible. Ideal point detectors would measure the point-dose accurately; however, a few point detectors will not enable verification of the intensity modulated beam in the various projections.

Ideal detectors do not exist and currently used measuring methods that have no time resolution and/or synchronisation or documentation to the treatment phase makes it impossible to apply relevant corrections to the measurement and thereby improve the result.

Direct measuring detectors currently used on the radiotherapy market are ionisation chambers and semiconductors. The ionisation chambers have in general a better long term stability than semiconductors. However, the spatial resolution of the ionisation chamber is rather limited, normally about 3-4 mm, which is a major limitation in the applications discussed herein.

Nearly 10 years ago scintillation detectors were proposed for radiation therapy, but is has however not been possible to make this technology work in practice. One of the main reasons is that the PM tube or photodiode that is used to convert the light to an electric signal must be kept out of the primary beam and the fibre optics used to connect the scintillation detectors to the PM tube or the photodiode creates scintillations as well. Proposals using dummy fibre optics has been presented, but the underlying technical problems has not been possible to solve.

Semiconductors are mainly diodes or MOSFET detectors. Both these types are based on silicon and thereby they have the same or similar energy dependency. Both have a high specific efficiency measuring radiation, which is an important parameter when measuring small doses. In "Investigation of the use of MOSFET for clinical IMRT dosimetric verification," Chuang, F. Cynthia, et. al., Med. Phys. 29(6), June 2002, a MOSFET detector system for IMRT verification is disclosed. This system provides for an easy calibration and an instantaneous read-out of test results but shows reproducibility, linearity, energy and angular responses similar to that of conventional dosimeters. The major drawback with the disclosed MOSFET detector system is however the limited lifespan of the detectors, which is mainly caused by radiation damage. Normally, the tolerance against radiation damage is approximately 200 Gy for a MOSFET detector. Moreover, the absorbed dose in a MOSFET can be read directly or after use, but not in real time applications.

Diodes are very reliable detectors with a high tolerance against radiation damage that exceeds 200000 Gy, i.e. approximately 1000 times higher in comparison with a MOSFET. Both MOSFET detectors and ionisation chambers require a bias, which complicates a system with an extensive number of detectors. Diodes are generally very reliable detectors and are used in many applications, e.g., integrating measurements as in vivo dosimetry and output factor measurements in small fields respectively real-time measurement, e.g., relative measurement in water phantoms. The main limitation is the energy dependence and the long term stability even though the latter has been improved during the recent years.

SUMMARY

Thus, an object of the present invention is to provide an efficient pre-treatment measurement method that sufficiently and accurately verifies the dose distribution from a complete treatment fraction (all beam projections) to be delivered to a patient.

It is a further object of the present invention is to provide tools to find the causes of deviations compared to a treatment plan.

These and other objects are achieved according to the present invention by providing methods, a computer readable medium, and a detector configuration having the features defined in the independent claims.

Preferable embodiments of the invention are characterised by the dependent claims.

According to a first aspect, there is provided a method of measuring dose distribution in a phantom for radiation therapy treatment verification, wherein at least two detector planes are arranged in said phantom in a non-parallel manner, each plane being provided with a plurality of diode detectors, wherein said phantom is irradiated using a patient specific treatment. The method comprises the steps of obtaining information regarding the dose distribution inside said phantom by performing measurements using said detectors, dividing the measurements in time-intervals; and using said information in the treatment verification.

According to a second aspect, there is provided a detector configuration in a phantom suitable for radiation therapy, comprising at least two detector planes provided with a plurality of diode detectors for measuring irradiation in said phantom, said irradiation being delivered using a patient specific treatment. The planes are arranged in a non-parallel manner, wherein said detectors has a thickness in a range less than the range of the electrons of the maximum energy in the range where the dependency is significant. According to a further aspect, there is provided a computer readable medium comprising instructions for bringing a computer to perform the method according to the first aspect of the invention.

Diode detectors are configured in two or more non-parallel planes in a phantom, e.g., body-phantom, (without connection to the gantry rotation, i.e., the rotation of the device applying the irradiation), and the measurement is divided in time-intervals. The special configuration of the detectors makes it possible to verify the intensity modulation across the beam in any beam projection and at the same time totalise the dose from all projections in the fixed measurement-points in the phantom. In addition, the overall measurement accuracy is significantly improved by dividing the measurement in time-intervals. This provides advantages compared to existing solutions. For example, a placement of the detectors in a 3D matrix would require an extensively increased number of detectors, which, in turn, would entail very high costs and which also would require significant processing times in order to process the information or data obtained from the detectors during the measurements. Furthermore, the division into time-interval enables use of individual correction factors for each time interval. In addition, this facilitates an evaluation of discrepancies in dynamic fields and/or ARC-therapy and reduces the directional and/or energy dependency of the detectors.

Preferably, the information obtained at the measurements of the dose distribution in the phantom is used at IMRT treatment verification.

The length of a time interval depends on the IMRT technique used as well as the size and change of correction factors. The case when a detector goes from being inside the field to outside is most important and it takes approximately 100 msec. Typical values for the time intervals are thereby in the range from 10 usec (one pulse, gating) to 100 msec. Thus, the time intervals are, defined from the required overall accuracy in dose determination. The dose contribution in each time interval can be totalised for the whole treatment as a first step to verify the complete treatment delivery, discrepancies can then be further analysed by comparisons at each field (projection) and sub fields. By totalising the dose from the intervals in various ways, a complete fraction, per field (projection), per sub field etc., the analysis can get deeper when required still using the same measurement data, and thereby, no updated measurement must be done which will save time and also make it possible to find intermittent errors.

According to an example embodiment, the dose measurements are synchronized with the delivered accelerator pulses. These are stored with the information on the current parameters of the treatment unit, e.g., projection. Measurements in short time-intervals (<100 msec) require a high detection efficiency per unit volume especially when the demands simultaneously is high on the spatial resolution, typically 1 mm. Using a silicon diode with the required size, the signal level generated outside the primary field is in the range of pA. Such small currents are difficult to handle with high accuracy and the electronic noise becomes significant. The therapy system delivers the dose in pulses at a frequency between 50 and 1000 Hz, each pulse having a length of less than 10 μsec and thereby the radiation is distributed during less than 10% of the time. By measuring only during the pulses, i.e., synchronizing the dose measurements with the delivered pulses, the noise can be reduced to a minimum and the dose can be measured at the required accuracy.

According to another example embodiment, the measurements are synchronized with the respiratory cycle of the patient for which the patent specific treatment is intended. External signals obtained by, for example, an X-ray unit, which indicates the phase of the respiratory cycle, e.g., used to turn the irradiation beam on and off, are stored with each measurement. Thereby, the dose delivered in the various phases of the respiratory cycle can be determined. The measured dose per pulse can be grouped in various time-intervals due to the requirements at the specific set-up. Furthermore, the IMRT treatment technique increases the requirement on reproducible patient positioning. The synchronisation with the respiratory cycle, so called respiratory gating, decreases the irradiation of healthy tissue. That is, the margins that are added in order to ensure that the tumour within the applied field can be reduced by using respiratory gating and thereby the proportion of irradiated healthy tissue can be decreased.

In addition, synchronizing measurements with delivered accelerator pulses can be utilized in combination with synchronization between the measurements and the respiratory pulses to verify that the dose is given at the correct phase of the respiratory cycle of the patient.

According to an example embodiment, correction factors are calculated according to $$Corr_{n, f, seg-n,f, p, t(i), t(i+1)} = C_{dir} * C_{depth} * C_{pos} \quad (1)$$

or $$Corr_{n, f, seg-n,f, p, t(i), t(i+1)} = C_{dir} + C_{depth} + C_{pos} \quad (2)$$

$Corr_{n, f, seg-n,f, p, t(i), t(i+1)}$ The correction factor to be used with detector-element n, in the sub-field, f in the phantom, correcting the measured dose integrated from time t(i) until t(i+1) to achieve the dose in the point of the detector n location.

$C_{dir}$ Factor correcting for any directional dependency in the detector $C_{depth}$ Factor correcting for any depth (energy and or dose rate) dependency in the detector $C_{pos}$ Factor correcting for any position (in primary beam, outside primary beam, edge of primary beam etc.) dependency in the detector According to an example embodiment, each detector plane may be provided with detectors having a thickness in a range less than the range of the electrons of the maximum energy in the range where the dependency is significant. (<200 keV corresponding to approximately 200 μm in silicon). Thereby, the energy and/or directional dependency of the detectors are reduced significantly, which mainly is caused by differences in the photons mass-attenuation in the detectors compared with the media they are arranged in.

As realized by the person skilled in the art, the technology may be realized or implemented as a computer program or a computer readable medium, preferably within the contents of the control and measurement system of the radiotherapy device, and thereby using the processor and storage means available there. Alternatively, it may be implemented in a stand-alone unit comprising the equipment such as a central processing unit CPU performing the steps. This is performed with the aid of a dedicated computer program, which is stored in the program memory. It is to be understood that the computer program may also be run on a general purpose industrial computer instead of a specially adapted computer.

Further objects and advantages will be discussed below.

BRIEF DESCRIPTION OF THE DRAWINGS

In the following detailed description, reference will be made to the accompanying drawings, of which FIG. 1a schematically shows a treatment machine to which a phantom is arranged, which in turn is provided with detectors, FIG. 1b schematically shows the arrangement of FIG. 1a but with a human body instead of the phantom, FIG. 2. schematically shows a typical example on a body shaped phantom with two crossing planes with detectors in a special arrangement to optimise the number of detectors.

FIG. 3. schematically shows various beam directions (projections) towards the body shaped phantom.

DETAILED DESCRIPTION

Figure 4C:
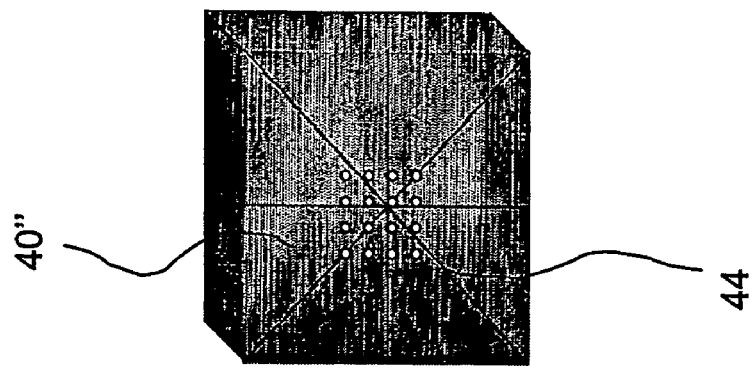
FIGS. 4a-4c. schematically shows different examples of patterns for arranging the detectors on the detector planes.

A radiotherapy device (gantry) utilised for treating tumours with radiation are shown schematically in FIGS. 1a and 1b and is generally denoted with reference numeral 10. The device comprises a radiotherapy system capable of emitting a beam 12 of electrons or photons from a treatment head. The radiotherapy system is provided with a conventional field-shaping device (not shown), for example an MLC, for allowing the lateral shape of the beam to be altered so as to shield off non-affected areas of the body, intensity modulate the beam, and concentrate the beam to the tumour. The radiotherapy system comprises control and measurement means (not shown) including processor and storage means, for example, a central processing unit CPU for performing the steps of the method according to the invention.

A treatment couch 16 is arranged for a patient 14 to lie on, see FIG. 1b. The couch can rotate around a vertical axis, and move horizontally, vertically and longitudinally in order to place the area to be treated of the patient in the area of the beam.

Further, detectors are placed inside a phantom, e.g., a body-phantom, in a way that reduces the number of detectors and still enables verification of the intensity modulated beams in all projections and simultaneously measures total dose distribution from all beam-projections in fixed points in the treated volume.

Preferably, the detectors are arranged in two or more non-parallel planes arranged in such a way that the crossing point of the planes is located in the vicinity of the rotation point of the treatment machine, preferably within 5 cm from the rotation point, and that either of the detector-planes covers the whole cross section of the beam in any projection FIGS. 2 and 3. FIG. 2 shows detector-planes 20 and 21 placed inside the phantom 22 with detectors configured in lines 23 and in an area 24 and FIG. 3 is an illustration of typical beam directions 30 irradiating the phantom from different projections.

Figure 4B:
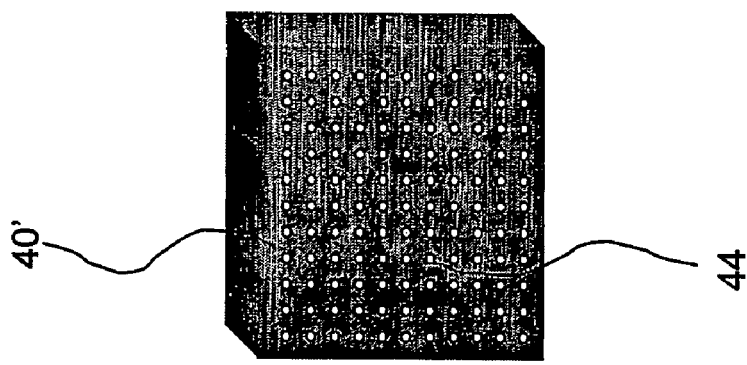
Figure 4A:
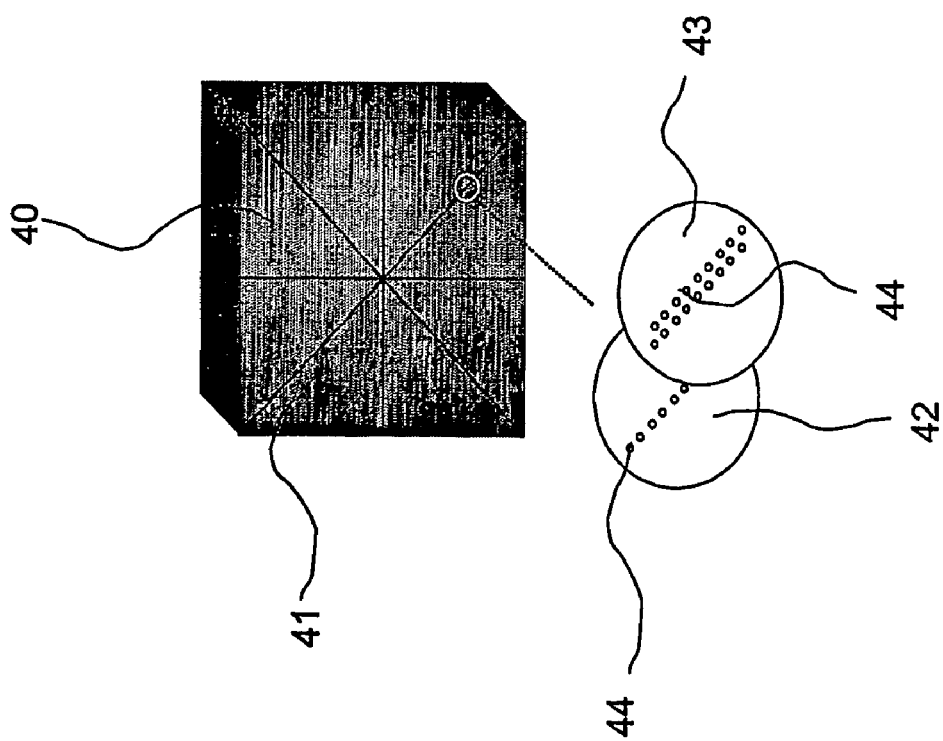

FIGS. 4a-4c schematically show different examples of detector patterns on detector planes 40, 40' and 40", respectively. FIG. 4a shows a detector plane 40 provided with a number of detectors lines 41, each line 41 represents an one dimensional (1D) array 42 of detectors 44 or a zigzag pattern 43 of detectors 44. FIG. 4b shows a detector plane 40' provided with detectors 44 arranged according to a two dimensional array, i.e. a matrix of detectors 44. FIG. 4c shows a detector plane 40" provided with detectors 44 arranged according to an example combination of the configurations shown in FIGS. 4a and 4b.

The above-mentioned equipment is used to enable measurement and verification of dose delivery in radiotherapy treatment, in particular prior to applying the treatment on the patient (pre-treatment verification). The measured dose distribution is compared with the dose distribution from the planned treatment of the specific patient after recalculating it to a similar phantom as the measurement phantom.

A typical example sequence from diagnostics to IMRT treatment is described below:

An individual treatment plan for the patient is made using a Treatment Planning System (TPS). The anatomy of the patient has first been defined using diagnostic equipment, e.g., CT, Computerised Tomography, and the radiation characteristics of the treatment device are defined generally by measurements imported in the TPS. The target-volume and risk-organs are defined, and then the optimum plan for the treatment is made where criteria such as maximum dose to the risk-organs and the minimum dose to the target etc. are used. The outcome of the plan is information that will be used by the treatment machine to set projections, beam modality, field shapes, and movement of the MLC-leaves, etc.

The patient-specific treatment plan, in the TPS, is applied on a phantom, suitable for dose measurements, and the dose distribution inside the phantom, using the patient specific treatment, is calculated.

Prior to treatment, a physical phantom, identical to the one simulated in the calculation, is irradiated using the patient specific treatment. The dose distribution inside the phantom is measured and integrated per projection and for all projections, complete fraction.

The measured and the calculated dose distributions are compared to verify the delivery of the patient specific treatment.

Accordingly, information regarding the dose distribution inside the phantom is obtained by performing measurements using the detectors, which information is used in the treatment verification and/or stored.

Figure 5:
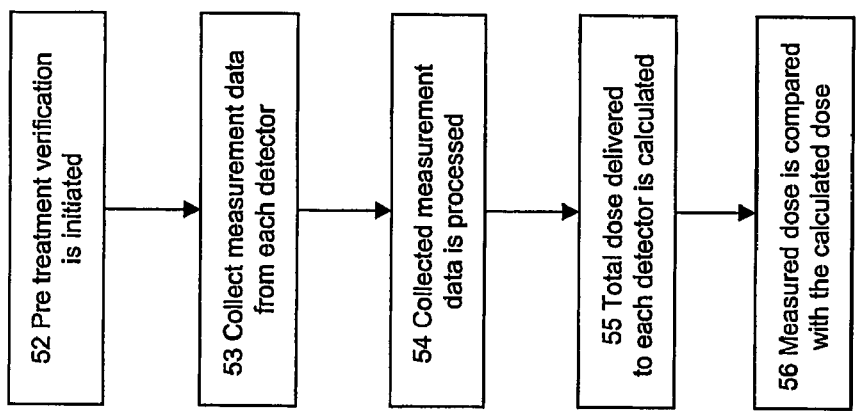
FIG. 5 schematically shows an example embodiment of the method of measuring dose distribution in a phantom for radiation therapy treatment verification.

Turning now to FIG. 5, an example method of measuring dose distribution in a phantom for radiation therapy treatment verification is described. Detector planes comprising a number of diode detectors arranged according to a detector pattern, for example, one of the patterns shown in one of FIGS. 4a-4c, are placed in the phantom. The phantom including the detectors is placed in the isocenter (rotation centre) of the treatment machine and aligned using positioning lasers in the treatment room. The measurements electronics are connected to a PC located in the control room, see FIG. 6. A connection between the treatment machine and the measurement electronics and/or via, for example, a LAN to the controlling PC might be established to synchronize the measurement and the delivery of the treatment. At step 52, the pre-treatment verification is initiated, i.e., the phantom is irradiated according to the patient specific treatment. Then, at step 53, the measurement data from each detector is collected for each time-interval. By using individual correction factors for each time-interval, a significant enhancement of the measurement accuracy is accomplished, see below. At step 54, after completed irradiation, or simultaneously, the data is processed and corrected using equations (1) or (2). Thereafter, at step 55, the total dose delivered to each detector is calculated. Further, the planed treatment is imported to the PC-SW. Then, at step 56, the measured dose is compared with the calculated dose. If the deviation exceeds a certain action-level, the calculated dose distribution in the treatment plan in each projection might be imported and the dose recalculated for each projection for comparison. If required, the comparison can be performed on sub-fields, (i.e., a part of a projection).

Figure 6:
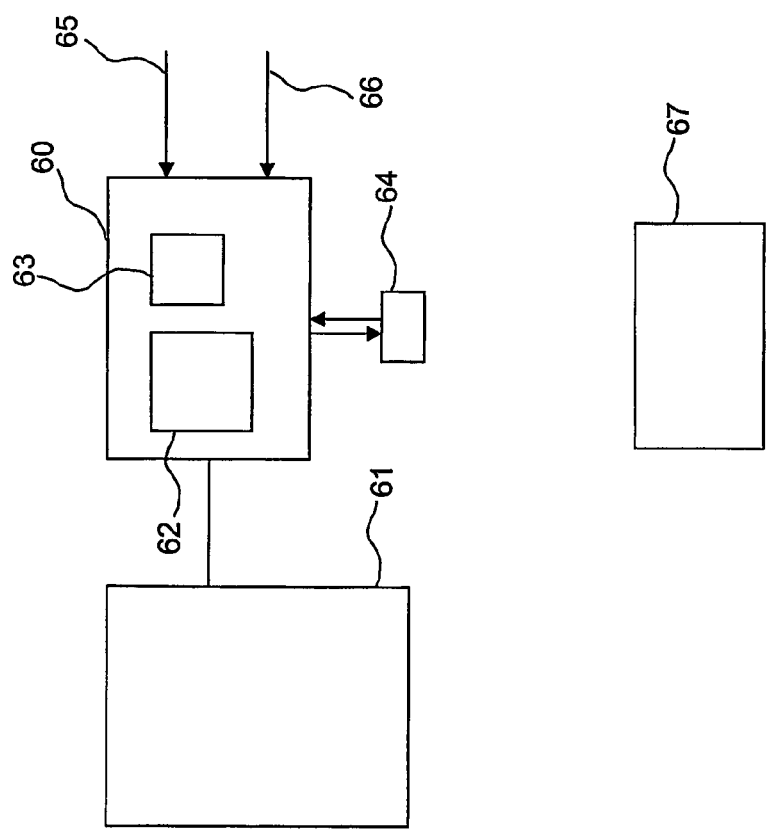
FIG. 6 schematically shows an example embodiment of a system in which the method of measuring dose distribution in a phantom for radiation therapy treatment verification can be employed.

With respect to FIG. 6, an example embodiment of a system in which the method of FIG. 5 can be implemented is shown. A reading unit 60 comprising a microprocessor 62 and storage 63 is connected to detector planes 61, see FIGS. 2, and 4a-4c. The reading unit 60 is arranged to record or measure the absorbed dose of each detector. The storage 63 may include a random access memory (RAM) and/or a non-volatile memory such as read-only memory (ROM). As will be appreciated by one of ordinary skill in the art, storage may include various types of physical devices for temporary and/or persistent storage of data which includes solid state, magnetic, optical and combination devices. For example, the storage may be implemented using one or more physical devices such as DRAM, PROMS, EPROMS, EEPROMS, flash memory, and the like. In addition, the reading unit 60 is provided with an input for receiving signals from the therapy system 65 and an input for receiving signals from external devices 66, such as an X-ray unit. By using the signals from the therapy system, the measurements can be synchronized with the delivered dose pulses. Moreover, by connecting an external device, such as an X-ray unit or a laser sensor, monitoring the respiratory cycle, the measurements can be synchronized with the respiratory cycle. Thereby, respiratory gating can be performed in order to decrease the irradiation of healthy tissue. That is, the margins that are added in order to ensure that the tumour without doubt is within the applied field can be reduced by using respiratory gating and thereby the proportion of irradiated healthy tissue can be decreased. Furthermore, the reading unit 60 is connected to communication means 64 for wireless communication of, for example, measurement data to an external processing unit 67, for example, an PC. In this embodiment, the communication means 64 is a LAN connection. The method may be implemented in the control and measurement system of the radiotherapy device. Alternatively it may be implemented in a stand-alone unit comprising the necessary equipment such as a central processing unit CPU performing the steps of the method, for example, in the personal computer 67. This is performed with the aid of a dedicated computer program, which is stored in the program memory. It is to be understood that the computer program may also be run on a general purpose industrial computer instead of a specially adapted computer.

The software includes computer program code elements or software code portions that make the computer perform the method using equations, algorithms, data and calculations described herein. A part of the program may be stored in a processor as above, but also in a ROM, RAM, PROM or EPROM chip or similar. The program in part or in whole may also be stored on, or in, other suitable computer readable medium such as a magnetic disk, CD-ROM or DVD disk, hard disk, magneto-optical memory storage means, in volatile memory, in flash memory, as firmware, or stored on a data server.

According to an example embodiment, the dose measurements are synchronized with the delivered accelerator pulses. These measurements are stored with the information on the current parameters of the treatment unit, e.g., projection. Measurements in short time-intervals (<100 msec) require a high detection efficiency per unit volume especially when the demands simultaneously are high on the spatial resolution, typically 1 mm. Using a silicon diode with the required size, the signal level generated outside the primary field is in the range of pA. Such small currents are difficult to handle with high accuracy and the electronic noise becomes significant. The therapy system delivers the dose in pulses at a frequency between 50 and 1000 Hz, each pulse having a length of less than 10 μsec and thereby the radiation is distributed during less than 10% of the time. By measuring only during the pulses, i.e., synchronizing the dose measurements with the delivered pulses, the noise can be reduced to a minimum, and the dose can be measured at the required accuracy.

According to another example embodiment, the measurements are synchronized with the respiratory cycle of the patient for which the patent specific treatment is intended. External signals obtained by, for example, an X-ray unit, which indicates the phase of the respiratory cycle, e.g., used to turn the irradiation beam on and off, is stored with each measurement. Thereby, the dose delivered in the various phases of the respiratory cycle can be determined. The measured dose per pulse can be grouped in various time-interval due to the requirements at the specific set-up. Furthermore, the IMRT treatment technique increases the requirement on reproducible patient positioning. The synchronization with the respiratory cycle, so called respiratory gating, decreases the irradiation of healthy tissue. That is, the margins that are added in order to ensure that the tumour is within the applied field can be reduced by using respiratory gating and thereby the proportion of irradiated healthy tissue can be decreased.

In addition, synchronizing measurements with delivered accelerator pulses can be utilized in combination with synchronization between the measurements and the respiratory pulses to verify that the dose is given at the correct phase of the respiratory cycle of the patient.

As indicated above, a further enhancement of the measurement accuracy can be accomplished by dividing the measurements in short time-intervals and using individual correction factors for each time-interval. The length of a time interval depends on the IMRT technique used as well as the size and change of the correction factors. Thus, the time intervals are defined from the required overall accuracy in the dose determination. The dose contribution in each time interval can be totalled for the whole treatment as a first step to verify the complete treatment delivery; discrepancies can then be further analysed by comparisons at each field (projection) and sub fields. According to preferred example embodiments, the correction factors are calculated according to $$Corr_{n,f,\,seg-n,f,\,p,\,t(i),\,t(i+1)} = C_{dir} \cdot C_{depth} \cdot C_{pos} \quad (1)$$

or $$Corr_{n,f,\,seg-n,f,\,p,\,t(i),\,t(i+1)} = C_{dir} + C_{depth} + C_{pos} \quad (2)$$

$Corr_{n,f,\,seg-n,f,\,p,\,t(i),\,t(i+1)}$ The correction factor to be used with detector-element n, in the sub-field, f in the phantom, correcting the measured dose integrated from time t(i) until t(i+1) to achieve the dose in the point of the detector n location.

$C_{dir}$ Factor correcting for any directional dependency in the detector $C_{depth}$ Factor correcting for any depth (energy and or dose rate) dependency in the detector $C_{pos}$ Factor correcting for any position (in primary beam, outside primary beam, edge of primary beam etc.) dependency in the detector Which one of (1) or (2) that is selected depends on how $C_{dir}$, $C_{depth}$ and $C_{pos}$ were obtained. Preferably, equation (1) is used when the correction factors are accepted to be independent of each other and, accordingly, can be obtained individually. Obtaining the correction factors using this equation is time efficient. Preferably, equation (2) is used if each combination of factors are to be measured. This method provides very accurate results.

If the diode-material differs in mass-density or electron-density from the phantom it might be selected to be thin, at least in one dimension, to reduce energy and directional dependency. Preferably, the detector is made thinner than the range of the electrons of the maximum energy in the range where the dependency is significant, e.g., for Si-detector in water the energy dependency is documented for photons with energy less than 200 keV where the electron range in Si is 200 um. The directional dependency is improved when Silicon is thinner than 500 um.

For a detector where all material except the sensitive part, is similar in mass-attenuation as the media it will measure in, only the sensitive part has to be thinner than the range of the electrons, for the maximum energy where the dependency is significant, in order to reduce the energy dependency.

For a detector where both the sensitive part and the surrounding material differ in mass-attenuation compared to the media it is arranged in, the sensitive part and the material that differs must be thin enough to reduce the energy dependency.

In addition, the "thin detector", i.e., a detector having a thickness made thinner than the range of the electrons of the maximum energy in the range where the dependency is significant, can preferably be used in several other applications such as: Water phantom dosimetry and in vivo dosimetry during Brachy therapy in Radio therapy. Water phantom dosimetry is performed using fixed detectors or detectors placed on a servo mechanism in a phantom filled with water. The system has several applications: acceptance tests of a treatment machine—general measurement of the dose distribution from the treatment machine; and measurement of the dose distribution in 3D. In vivo dosimetry during Brachy therapy (radioactive sources inserted into the human body) incorporates measurements inside the human body, interstitial or intra cavity e.g., thrachea, uterus, rectum, and bladder.

It is to be understood that the above description and the accompanying drawings are to be regarded as non-limiting examples and that the scope of protection is defined by the appended patent claims.

The invention claimed is:

1. A method of measuring dose distribution in a phantom for radiation therapy treatment verification, wherein at least two detector planes are arranged in said phantom in a non-parallel manner, each plane being provided with a plurality of diode detectors, wherein said phantom is irradiated using a patient specific treatment, comprising:
   obtaining information regarding the dose distribution inside said phantom by performing measurements using said detectors;
   dividing the measurements in time-intervals, each time-interval having maximum length of approximately 100 msec; and
   using said information in the treatment verification.

2. A method according to claim 1, wherein the information obtained by said measurements is used for IMRT verification.

3. A method according to claim 1, wherein said irradiation of the phantom comprises delivering dose pulses, the method further comprising synchronizing the measurements with said delivered doses.

4. A method according to claim 1, further comprising: synchronizing the measurements with a respiratory cycle of the patient for which the patient specific treatment is intended; and determining the dose delivered in the various phases of the respiratory cycle.

5. A method according to claim 1, further comprising the step of storing the data for each specific time-interval for measurements in said phantom.

6. A method according to claim 1, further comprising the step of calculating a correction factor for each detector element for each time-interval using said obtained information regarding the dose distribution inside said phantom.

7. A method according to claim 6, wherein each correction factor $Corr_{n, f, seg-n, f, p, t(i), t(i+1)}$ is calculated according to:

$$Corr_{n, f, seg-n, f, p, t(i), t(i+1)} = C_{dir} * C_{depth} * C_{pos},$$

where:
$Corr_{n, f, seg-n, f, p, t(i), t(i+1)}$ is the correction factor to be used with detector element n, in the sub field f in the phantom, correcting the measured dose integrated from time t(i) until t(i+1) to achieve the dose in the point of location of detector n, $C_{dir}$ is a factor correcting for any directional dependence in detector n, $C_{depth}$ is a factor correcting for any depth, energy and/or dose rate, in detector n, and $C_{pos}$ is a factor correcting for position dependency in detector n.

8. A method according to claim 6, wherein each correction factor $Corr_{n, f, seg-n, f, p, t(i), t(i+1)}$ is calculated according to:

$$Corr_{n, f, seg-n, f, p, t(i), t(i+1)} = C_{dir} + C_{depth} + C_{pos},$$

where:
$Corr_{n, f, seg-n, f, p, t(i), t(i+1)}$ is the correction factor to be used with detector element n, in the sub field f in the phantom, correcting the measured dose integrated from time t(i) until t(i+1) to achieve the dose in the point of location of detector n, $C_{dir}$ is a factor correcting for any directional dependence in detector n, $C_{depth}$ is a factor correcting for any depth, energy and/or dose rate, in detector n, and $C_{pos}$ is a factor correcting for position dependency in detector n.

9. A method according to claim 1, wherein the detector planes are arranged such that for each angle projection of a radiation beam used to irradiate said phantom, either of said non-parallel planes intersects with all parts of the radiation beam.

10. A method according to claim 1, wherein each detector plane is provided with detectors having a thickness in a range less than a range of electrons in a radiation beam used to irradiate said phantom where energy dependency is significant.

11. A detector configuration for use in the method according to claim 1, where the detector configuration is arranged in a phantom suitable for radiation therapy and comprises at least two detector planes provided with a plurality of diode detectors for measuring irradiation in said phantom, said irradiation being delivered using a patient specific treatment, wherein said planes being arranged in a non-parallel manner, wherein each of said detector planes has a thickness less than 500 μm.

12. Detector configuration according to claim 11, wherein each of said detector planes has a thickness of less than 200 μm.

13. Diode detector according to claim 1, wherein said detector is used in water phantom dosimetry or in vivo dosimetry during Brachy therapy in Radio therapy.

14. A computer-readable medium embodied in a tangible medium comprising instructions which when implemented by a computer, cause the computer to perform the steps of the method according to claim 1.

15. A method of measuring dose distribution in a phantom for radiation therapy treatment verification, wherein detector planes are arranged in said phantom, each plane being provided with a plurality of diode detectors, wherein said phantom is irradiated using a patient specific treatment, comprising:
   obtaining information regarding the dose distribution inside said phantom by performing measurements using said detectors;

dividing the measurements in time-intervals, each time-interval having a maximum length of approximately 100 msec;

synchronizing the measurements with a respiratory cycle of a patient for which the patient specific treatment is intended;

determining the dose delivered in the various phases of the respiratory cycle; and using said information in the treatment verification.

16. A method according to claim 15, wherein at least two detector planes are arranged in said phantom in a non-parallel manner.

17. An apparatus for measuring dose distribution in a phantom for radiation therapy treatment verification where said phantom is irradiated using a patient specific treatment, comprising:

at least two detector planes arranged in said phantom in a non-parallel manner, each plane being provided with a plurality of diode detectors, and electronic circuitry configured to:

obtain information regarding the dose distribution inside said phantom by performing measurements using said detectors;

divide the measurements in time-intervals, each time-interval having maximum length of approximately 100 msec; and use said information in the treatment verification.

18. The apparatus in claim 17, wherein irradiation of the phantom comprises delivered dose pulses, and wherein the electronic circuitry is configured to synchronize the measurements with said delivered doses.

19. The apparatus in claim 17, wherein the electronic circuitry is configured to:

synchronize the measurements with a respiratory cycle of the patient for which the patent specific treatment is intended, and determine the dose delivered in the various phases of the respiratory cycle.

20. The apparatus in claim 17, wherein the electronic circuitry is configured to calculate a correction factor for each detector element for each time-interval using said obtained information regarding the dose distribution inside said phantom.

21. The apparatus in claim 20, wherein the electronic circuitry is configured to calculate each correction factor $Corr_{n, f, seg-n, f, p, t(i), t(i+1)}$ according to:

$$Corr_{n, f, seg-n, f, p, t(i), t(i+1)} = C_{dir} * C_{depth} * C_{pos}, \text{ where:}$$

$Corr_{n, f, seg-n, f, p, t(i), t(i+1)}$ is the correction factor to be used with detector element n, in the sub field f in the phantom, correcting the measured dose integrated from time t(i) until t(i+1) to achieve the dose in the point of location of detector n, $C_{dir}$ is a factor correcting for any directional dependence in detector n, $C_{depth}$ is a factor correcting for any depth, energy and/or dose rate, in detector n, and $C_{pos}$ is a factor correcting for position dependency in detector n.

22. The apparatus in claim 20, wherein the electronic circuitry is configured to calculate each correction factor $Corr_{n, f, seg-n, f, p, t(i), t(i+1)}$ is calculated according to:

$$Corr_{n, f, seg-n, f, p, t(i), t(i+1)} = C_{dir} + C_{depth} + C_{pos}, \text{ where:}$$

$Corr_{n, f, seg-n, f, p, t(i), t(i+1)}$ is the correction factor to be used with detector element n, in the sub field f in the phantom, correcting the measured dose integrated from time t(i) until t(i+1) to achieve the dose in the point of location of detector n, $C_{dir}$ is a factor correcting for any directional dependence in detector n, $C_{depth}$ is a factor correcting for any depth, energy and/or dose rate, in detector n, and $C_{pos}$ is a factor correcting for position dependency in detector n.

23. The apparatus in claim 17, wherein the detector planes are arranged such that for each angle projection of a radiation beam used to irradiate said phantom, either of said non-parallel planes intersects with all parts of the radiation beam.

24. An apparatus for measuring dose distribution in a phantom for radiation therapy treatment verification, wherein detector planes are arranged in said phantom, each plane being provided with a plurality of diode detectors, wherein said phantom is irradiated using a patient specific treatment, comprising:

means for obtaining information regarding the dose distribution inside said phantom by performing measurements using said detectors;

means for dividing the measurements in time-intervals, each time-interval having a maximum length of approximately 100 msec;

means for synchronizing the measurements with a respiratory cycle of a patient for which the patient specific treatment is intended;

means for determining the dose delivered in the various phases of the respiratory cycle; and means for using said information in the treatment verification.

* * * * *